(12) United States Patent
Leeton (10) Patent No.: US 10,654,033 B2
(45) Date of Patent: May 19, 2020

(54) VERTICAL SEPARATION VESSEL FOR IONIC LIQUID CATALYZED EFFLUENT

(71) Applicant: UOP LLC, Des Plaines, IL (US)

(72) Inventor: Eric Leeton, Corpus Christi, TX (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/986,290

(22) Filed: May 22, 2018

(65) Prior Publication Data

US 2018/0264451 A1 Sep. 20, 2018

Related U.S. Application Data

(63) Continuation of application No. PCT/US2016/061040, filed on Nov. 9, 2016.

(60) Provisional application No. 62/259,382, filed on Nov. 24, 2015.

(51) Int. Cl.
| | |
|---|---|
| *B01J 31/40* | (2006.01) |
| *B01D 17/02* | (2006.01) |
| *B01D 17/04* | (2006.01) |
| *C07C 7/00* | (2006.01) |
| *C10G 53/04* | (2006.01) |
| *B01J 31/02* | (2006.01) |

(52) U.S. Cl.
CPC ............ *B01J 31/40* (2013.01); *B01D 17/0211* (2013.01); *B01D 17/0214* (2013.01); *B01D 17/045* (2013.01); *B01D 17/047* (2013.01); *C07C 7/00* (2013.01); *C10G 53/04* (2013.01); *B01J 31/0277* (2013.01); *Y02P 20/582* (2015.11)

(58) Field of Classification Search
CPC ... B01J 31/40; B01J 31/0277; B01D 17/0214; B01D 17/047; B01D 17/045; B01D 17/0211; C10G 53/04; C07C 7/00; Y02P 20/582

See application file for complete search history.

(56) References Cited

U.S. PATENT DOCUMENTS

| | | |
|---|---|---|
| 2,417,106 A | 3/1947 | Frey |
| 3,879,487 A | 4/1975 | Vora |
| 3,894,111 A | 7/1975 | Anderson |
| 4,111,806 A | 9/1978 | Wright et al. |

(Continued)

FOREIGN PATENT DOCUMENTS

| | | |
|---|---|---|
| CA | 2044074 A1 | 1/1992 |
| CN | 1785940 A | 6/2006 |

(Continued)

OTHER PUBLICATIONS

CYTEC, Phosphonium Salts & Ionic Liquids, webpage printed Jul. 7, 2015.

(Continued)

*Primary Examiner* — Ali Z Fadhel (57) ABSTRACT

A separation vessel for separating an effluent stream that comprises a mixture of hydrocarbons and ionic liquid. The separation vessels may be vertically orientated. Ionic liquid is utilized to remove entrained ionic liquid droplets form rising hydrocarbons within the separation zone. The ionic liquid may be provided with a stream of the ionic liquid from the separation vessel. The ionic liquid may be provided as a layer or travel counter-current to the hydrocarbons rising in the separation vessel.

18 Claims, 4 Drawing Sheets

(56) References Cited

U.S. PATENT DOCUMENTS

| | | | | |
|---|---|---|---|---|
| 4,228,001 | A | * | 10/1980 | Carlson .................... B01J 47/10 210/189 |
| 4,275,032 | A | | 6/1981 | Anderson |
| 5,759,937 | A | * | 6/1998 | Hovis ..................... B01J 27/32 502/35 |
| 5,824,832 | A | | 10/1998 | Sherif et al. |
| 7,446,238 | B2 | | 11/2008 | Hovis et al. |
| 7,935,320 | B2 | | 5/2011 | Hovis et al. |
| 8,067,656 | B2 | | 11/2011 | Luo et al. |
| 2006/0173231 | A1 | | 8/2006 | Hovis et al. |
| 2007/0249486 | A1 | | 10/2007 | Elomari et al. |
| 2010/0130799 | A1 | * | 5/2010 | Ahmed ............... B01J 31/0277 585/311 |
| 2010/0130800 | A1 | * | 5/2010 | Luo ..................... B01D 17/045 585/446 |
| 2013/0066130 | A1 | | 3/2013 | Lou et al. |
| 2014/0163293 | A1 | | 6/2014 | Aiken et al. |
| 2015/0274614 | A1 | * | 10/2015 | Buchbinder ......... B01D 17/047 585/802 |

FOREIGN PATENT DOCUMENTS

| | | |
|---|---|---|
| CN | 101148392 A | 3/2008 |
| CN | 102091670 A | 6/2011 |
| CN | 102146051 A | 8/2011 |
| EA | 200901437 A1 | 4/2010 |
| EP | 0465161 A1 | 6/1991 |
| EP | 384457 | 4/1994 |
| RU | 2403965 | 3/2009 |
| WO | 0054867 | 9/2000 |

OTHER PUBLICATIONS

Matsumiya et al., "Electrochemical Behaviour of Hydrogen in Low-Viscosity Phosphonium Ionic Liquids", Z. Naturforsch, 66a1 pp. 668-674 (2011).

Tsunashima et al., "Physiochemical Properties of Trialkylphosphonium-Based Protic Ionic Liquids", The Electrochemical Society of Japan, 80(11), pp. 904-906 (2012).

International Search Report from corresponding PCT application No. PCT/US2016/061040, dated Jan. 26, 2017.

* cited by examiner

VERTICAL SEPARATION VESSEL FOR IONIC LIQUID CATALYZED EFFLUENT

CROSS-REFERENCE TO RELATED APPLICATIONS

This application is a Continuation of copending International Application No. PCT/US2016/061040 filed Nov. 9, 2016, which application claims priority from U.S. Provisional Application No. 62/259,382 filed Nov. 24, 2015, the contents of which cited applications are hereby incorporated by reference in their entirety.

FIELD OF THE INVENTION

The invention relates to a separation vessel for use with effluents containing ionic liquid, preferably from an alkylation process, and more particularly, the invention relates to a vertically orientated separation vessel.

BACKGROUND OF THE INVENTION

Ionic liquids are essentially salts in a liquid state, and are described in U.S. Pat. Nos. 4,764,440, 5,104,840, and 5,824,832. The properties vary extensively for different ionic liquids, and the use of ionic liquids depends on the properties of a given ionic liquid. Depending on the organic cation of the ionic liquid and the anion, the ionic liquid can have very different properties. The behavior of the ionic liquid varies considerably for different temperature ranges, and it is preferred to find ionic liquids that do not require operation under more extreme conditions such as refrigeration.

Ionic liquids have been used to catalyze a variety of hydrocarbon conversion processes, such as alkylation, isomerization, disproportionation, and the like. When ionic liquids are used to catalyze hydrocarbon conversion processes, the ionic liquid catalyst is typically dispersed into droplets to provide intimate contact between the various reactants. The mixture of ionic liquid, reactants and products are typically separated by gravity into two phases, a heavier ionic liquid phase and a lighter hydrocarbon phase. It is common for the hydrocarbon phase to include fine droplets of ionic liquid. As a result of the relatively high cost of ionic liquids, it is generally desirable to recover this entrained ionic liquid.

Conventional separation vessels comprise horizontally disposed vessels that allow the effluent to settle into the two phases and typically use coalescing medium or other elements to try and remove and/or recover the entrained droplets of ionic liquid contained within the hydrocarbon phase. While these conventional separation vessels and methods are believed to be effective for their intended purposes, there may be drawbacks associated with same.

For example, the horizontal vessels require a relatively large amount of plot space given the required time necessary for separating the effluent into the two phases. While this may not be a drawback for all applications and uses of such separation vessels, some locations may lack the requisite space for such vessels. Additionally, a coalescing media, which is typically required to remove the entrained ionic liquid from the hydrocarbon phase, may become fouled or plugged over time. This may impact the flow of fluids therethrough, as well as require maintenance or repairs to address—which requires equipment or unit shutdown resulting a loss of production and increased costs.

Accordingly, the present invention is directed at providing a separation vessel that addresses one or more of these drawbacks associated with the conventional separation vessels used for separating an effluent having ionic liquid.

SUMMARY OF THE INVENTION

One or more separation vessels have been invented for separating an effluent of an ionic liquid catalyzed reaction. The invented separation vessels require a smaller plot area as the vessel has a vertical orientation rather than a horizontal orientation. Additionally, the invented vessels utilize a layer of ionic liquid to remove entrained ionic liquid droplets from the up-flowing hydrocarbon phase.

Accordingly, in a first aspect of the present invention, the present invention may be characterized broadly as providing a separation zone for separating a hydrocarbon phase and an ionic liquid phase comprising: a separation vessel having an outlet for an ionic liquid stream, an outlet for a hydrocarbon effluent stream, and, an inlet for an effluent stream; at least one ionic liquid distribution member disposed in the separation vessel between the outlet for the hydrocarbon effluent stream and the inlet for the effluent stream, the at least one ionic liquid distribution member configured to allow up-flowing fluid to pass through the at least one ionic liquid distribution member and contact ionic liquid; and, a line configured to pass ionic liquid to the separation vessel above the at least one ionic liquid distribution member.

The separation vessel may comprise a vertically orientated separation vessel.

The separation zone may further comprise a pump configured to pass the ionic liquid stream from the separation zone to a reaction zone. The pump may be configured to pass ionic liquid to the separation vessel.

The separation zone may further comprise a flow directing baffle disposed inside of the separation vessel and configured to change a direction of flow of fluid within the separation vessel. The flow directing baffle may be disposed proximate the inlet for the effluent stream.

The separation vessel may comprise an upper portion with a first diameter and a lower portion with a second diameter being smaller than the first diameter.

The separation zone may further comprise a plurality of ionic liquid distribution members disposed in the separation vessel between the outlet for the hydrocarbon effluent stream and the inlet for the effluent stream. The ionic liquid distribution members may each comprise a tray. Each tray may comprise a plurality of passageways for the up-flowing fluid and a downcomer, and the downcomers of adjacent trays may be staggered in relation to each other. An uppermost tray may be configured to receive ionic liquid via the line configured to pass ionic liquid to the separation vessel.

In another aspect of the present invention, the present invention may be characterized broadly as providing a separation zone for separating a hydrocarbon phase and an ionic liquid phase comprising: a vertically orientated separation vessel having an outlet for an ionic liquid stream, an outlet for a hydrocarbon effluent stream, and, an inlet for an effluent stream; a plurality of ionic liquid distribution members disposed in the separation vessel between the outlet for a hydrocarbon effluent stream and the inlet for the effluent stream, each ionic liquid distribution member configured to allow up-flowing fluid to pass through the at least one ionic liquid distribution member and contact ionic liquid; a pump configured to pass the ionic liquid stream from the separation zone to a reaction zone; and, a line configured to pass ionic liquid from the pump back to the vertically orientated separation vessel.

The ionic liquid from the line may be passed into the vertically orientated separation vessel at a position above an uppermost ionic liquid distribution member and below the outlet for the hydrocarbon effluent stream. Each ionic liquid distribution member may further comprise a downcomer.

The separation vessel may comprise an upper portion with a first diameter and a lower portion with a second diameter being smaller than the first diameter. The separation zone may further comprise a flow directing baffle configured to change a direction of flow of fluid within the separation vessel.

The separation vessel may further comprise a conical portion disposed between the upper portion and the lower portion, and wherein the baffle is disposed in the conical portion.

In a further aspect of the present invention, the present invention may be characterized broadly as providing a process for separating an effluent including ionic liquid catalyst by: passing a reactor effluent stream from a reaction zone to a vertical separation vessel, wherein the separation vessel comprises an upper portion with a first diameter and a lower portion with a second diameter being smaller than the first diameter and a conical portion disposed between the upper portion and the lower portion; separating the reactor effluent stream into an ionic liquid phase and a hydrocarbon phase; passing a first portion of the ionic liquid phase to the reaction zone; and, removing ionic liquid droplets entrained in the hydrocarbon phase in the vertical separation vessel by contacting the hydrocarbon phase with ionic liquid disposed within the upper portion of the vertical separation vessel.

A layer of ionic liquid may be disposed on an ionic liquid distribution member within the upper portion of the vertical separation vessel.

The vertical separation vessel may comprise a plurality of ionic liquid distribution members. The process may further comprise passing a second portion of the ionic liquid phase from the lower portion of the vertical separation vessel to the upper portion of the vertical separation vessel.

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing figures, in which.

DETAILED DESCRIPTION OF THE INVENTION

As mentioned above, one or more separation vessels have been invented for separating an effluent stream that comprises a mixture of hydrocarbons and ionic liquid. The separation vessels of the present invention require less plot space, allowing for ionic liquid catalyzed reactions to be utilized in areas with small or limited space. Additionally, to minimize the amount of entrained ionic liquid droplets, a simple and robust design is utilized in which ionic liquid, for example, a slip stream of the ionic liquid from the separation vessel, is passed back into the vessel. As the hydrocarbon phase rises within the separation vessel, it will contact the ionic liquid resulting in the entrained ionic liquid droplets being removed. Such a design is less prone to fouling and is, thus, believed to require less maintenance. Finally, the separation vessels of the present invention can further save costs for operators by allowing the use of existing separation vessels to be retrofitted.

With these general principles in mind, one or more embodiments of the present invention will be described with the understanding that the following description is not intended to be limiting.

Figure 1:
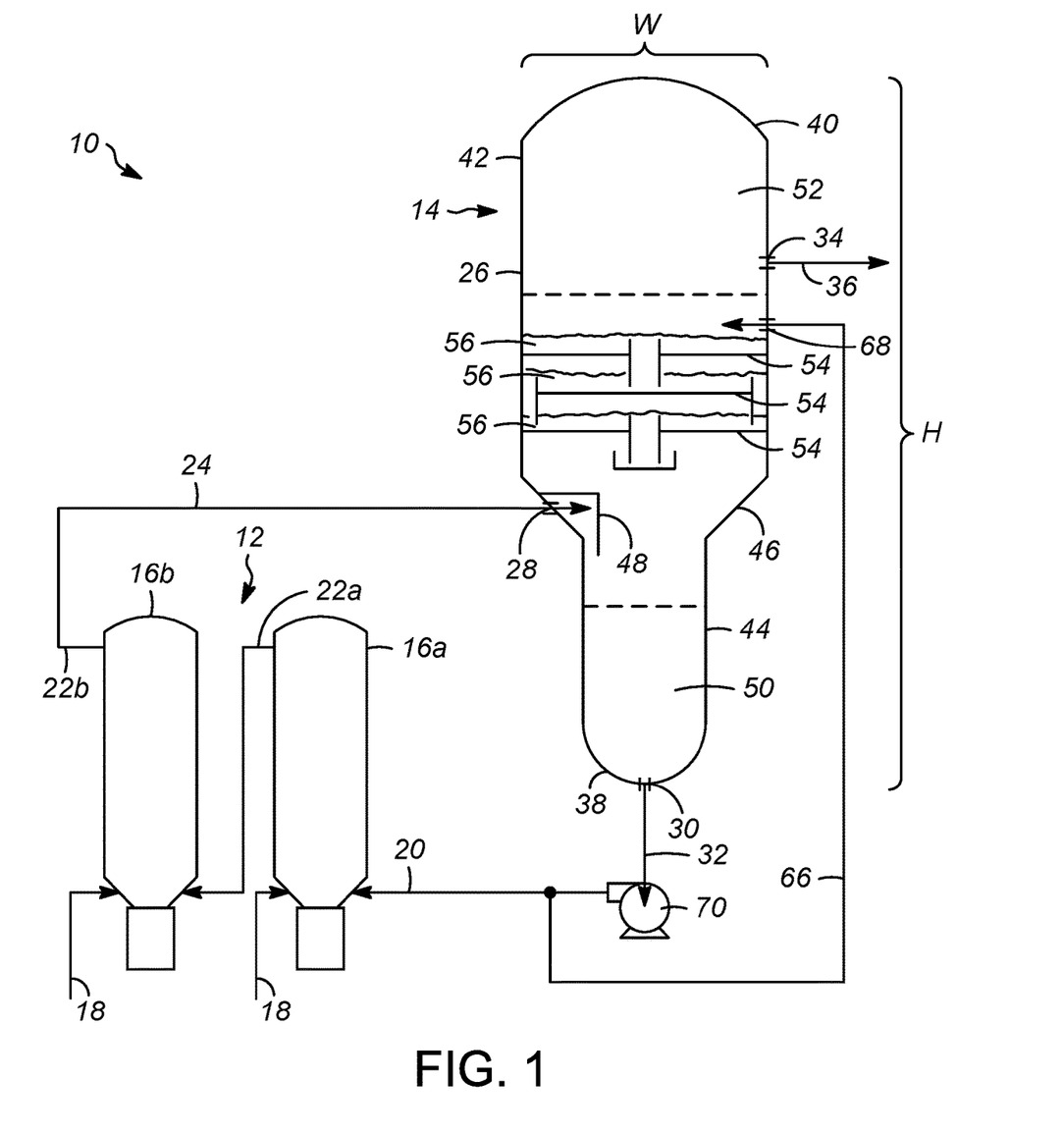
FIG. 1 shows a schematic flow diagram of a reactor system having a separation vessel occurring to one or more embodiments of the present invention.

As shown in FIG. 1, an ionic liquid reactor system 10 typically comprises a reaction zone 12 and a separation zone 14. The reaction zone 12 may have one or more reactors 16a, 16b which may be arranged in series. For example, at least one reactant stream 18, which may include a mixture of a recycle stream and a fresh feed stream, are passed into the first reactor 16a along with a stream of ionic liquid 20 which catalyzes a reaction between the reactants. An effluent stream 22a, comprising a mixture of products, ionic liquid and unreacted reactants is provided by the first reactor 16a. The effluent stream 22a from the first reactor 16a may be passed to the second reactor 16b. Another reactant stream 18, comprising, for example, fresh reactants, recycle reactants, or a mixture thereof, may also be passed to the second reactor 16b. Since the effluent stream 22a from the first reactor 16a includes ionic liquid, the effluent stream 22a from the first reactor 16a may also comprise a stream of ionic liquid. Again, within the second reactor 16b, the reactants will react, in the presence of the ionic liquid catalyst, and provide an effluent stream 22b.

In order to ensure proper mixing of the ionic liquid and the hydrocarbon reactants, the reactors 16a, 16b may include one or more mixing devices (not shown) such as impellers, mixing blades or other similar structures that are configured to mix the fluids, as well as disperse the ionic liquid into droplets. The particular design and arrangement of the reaction zone 12 is not important for the practicing of the present invention so long as it provides a net effluent stream 24 comprising a mixture of products, ionic liquid, and unreacted reactants. The net effluent stream 24 is passed from the reaction zone 12 to the separation zone 14.

As shown in FIG. 1, the separation zone 14 comprises a separation vessel 26 that includes an inlet 28 for the net effluent stream 24, an outlet 30 for an ionic liquid stream 32, and an outlet 34 for a hydrocarbon effluent stream 36. Since ionic liquid is heavier than hydrocarbons, it has a tendency to separate from the mixture and flow downward. In order to utilize and/or accommodate the separation tendency of the ionic liquid and hydrocarbons, it is preferred that the outlet 30 for the ionic liquid stream 32 is disposed proximate a bottom 38 of the separation vessel 26, and that the outlet 34 for the hydrocarbon effluent stream 36 is disposed proximate a top 40 of the separation vessel 26. The inlet 28 for the net effluent stream 24 is preferably disposed between the two outlets 30, 34.

Although it is not required, it is preferred that the separation vessel 26 comprises a vertically oriented separation vessel, in which that the separation vessel 26 is has a height H that is much greater than a width W of the separation vessel 26. Such a configuration is particularly beneficial in reactor systems 10 in which plot space is limited.

Figure 2:
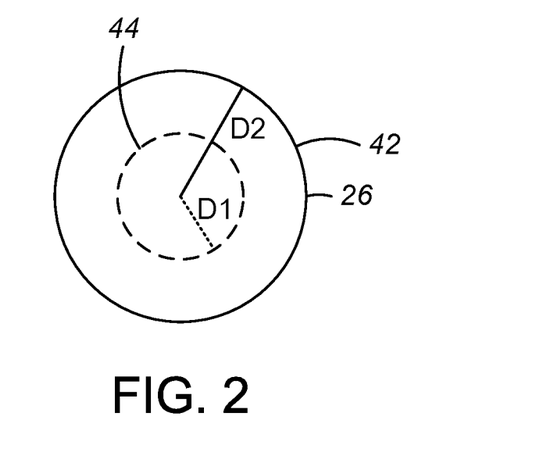
FIG. 2 shows a top view of the separation vessel shown in FIG. 1.

Additionally, as shown in FIG. 2, the separation vessel 26 may have an upper portion 42 with a first horizontal cross section, for example a circle, and a lower portion 44 with a second horizontal cross section smaller than the first horizontal cross section. Additionally, the lower portion 44 may have a diameter D1 that is smaller than a diameter of the upper portion 42. This configuration provides the separation vessel 26 with a smaller size on the bottom and a larger size on the top. Such a design is believed to be particularly beneficial to allow the reactor systems 10 to utilize less ionic liquid. As mentioned above, the ionic liquid can be expensive and the ability to operate with a smaller inventory is believed to be beneficial and/or desirable. As shown in FIG. 1, the upper and lower portions 42, 44 may be connected with by a sloped or conical portion 46.

Continuing on in FIG. 1, the net effluent stream 24 may be passed into the separation vessel 26 at the inlet 28 for the net effluent stream 24. Preferably, a flow directing baffle 48 or other similar structure is used to change the flow of the net effluent stream 24 after it is has been injected into the separation vessel 26. Most preferably, the flow directing baffle 48 changes the flow from a generally horizontal flow (as a result of being injected into the separation vessel 26) to a vertical flow (preferably downward). The flow directing baffle 48 may comprise any structure such as a baffle, impingement plate, vane, or the like.

Inside of the separation vessel 26, the heavier ionic liquid will fall towards the bottom 38 of the separation vessel 26, while the lighter hydrocarbons will rise towards the top 40 of the separation vessel 26. This will create at least two phases in the separation vessel 26, an ionic liquid phase 50 and a hydrocarbon phase 52. The ionic liquid phase 50 may be withdrawn, for example, by a pump 70, and passed back to the reaction zone 12. The hydrocarbon phase 52 may be passed, as is known, to a product recovery zone (not shown) having, for example, a fractionation column configured to separate the hydrocarbon effluent stream 36 into various hydrocarbon components including products and reactants.

As mentioned above, as the hydrocarbons flow upwards in the separation vessel 26, the hydrocarbons typically include entrained ionic liquid droplets. Accordingly, in order to recover same, at least one ionic liquid distribution member 54 is disposed within the separation vessel 26, preferably between the outlet 34 for the hydrocarbon effluent stream 36 and the outlet 30 for the ionic liquid stream 32. The ionic liquid distribution member 54 is configured to allow up-flowing fluid, such as the hydrocarbons, to pass through the ionic liquid distribution member 54. As the up-flowing fluid passes through the ionic liquid distribution member 54 it will contact ionic liquid associated with the ionic liquid distribution members 54. As a result of the contact, entrained droplets of ionic liquid in the hydrocarbons may be removed from the up-flowing hydrocarbons. Preferably, in order to minimize the amount of ionic liquid that is in the hydrocarbon effluent stream 36, the separation vessel 26 includes a plurality of ionic liquid distribution members 54 configured such that up-flowing fluid must pass through multiple ionic liquid distribution members 54 before being withdrawn from the separation vessel 26.

Figure 3:
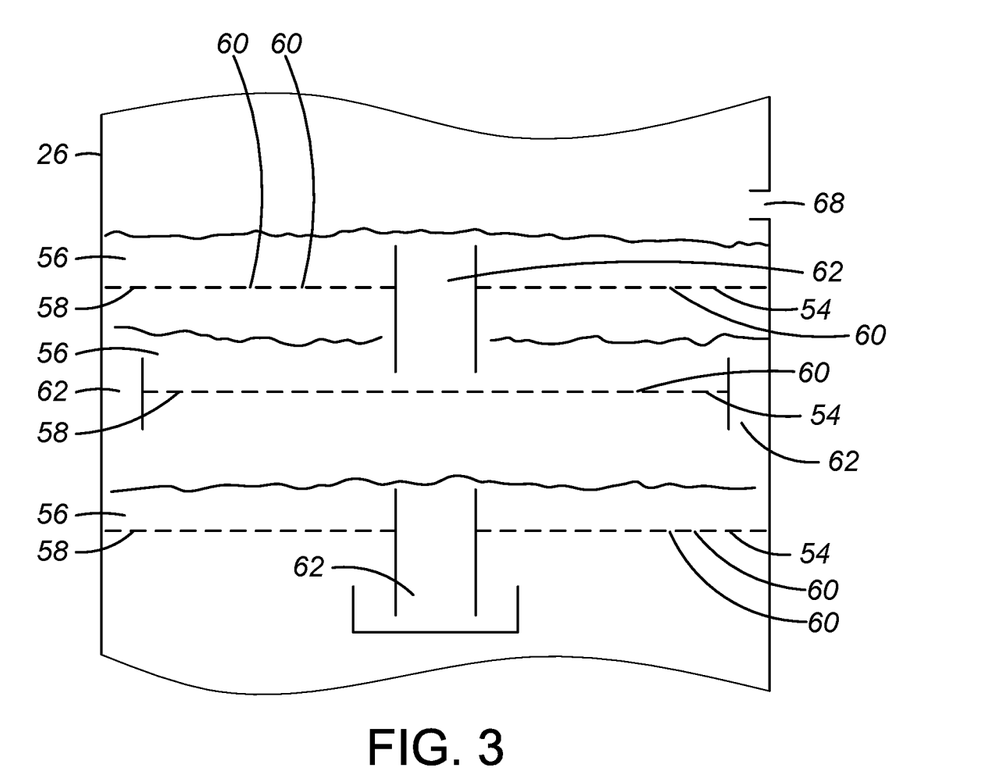
FIG. 3 shows a side view of a portion of the separation vessel shown in FIG. 1.

As shown in FIG. 3, the ionic liquid distribution member (s) 54 may provide a layer 56 of ionic liquid and the up-flowing hydrocarbons may pass through the layer 56 of ionic liquid. For example, the ionic liquid distribution member(s) 54 may comprise a tray 58 having a plurality of passageways 60 for the up-flowing fluid and at least one downcomer 62. Exemplary trays 58 include sieve type trays, bubble cap trays, valve trays, or the like. Entrained ionic liquid droplets in the hydrocarbons may be removed when contacted with the layer 56 of ionic liquid on the trays 58.

In embodiments with ionic liquid distribution members 54 or trays 58 having downcomers 62, it is preferred that the downcomers 62 of adjacent ionic liquid distribution members 54 may be staggered, or offset, to promote flow across the ionic liquid distribution members 54. For example, as shown in FIG. 3, the downcomer 62 of one tray 58 may be disposed proximate a center of the tray 58, while the downcomer 62 of an adjacent tray is disposed proximate an outer periphery of the tray 58. As the thickness of each layer 56 exceeds the height of the downcomer 62, the ionic liquid can pass down through the downcomer 62 into the next ionic liquid distribution member 54. Thus, by staggering the downcomers 62, the flow of ionic liquid is promoted.

Figure 4:
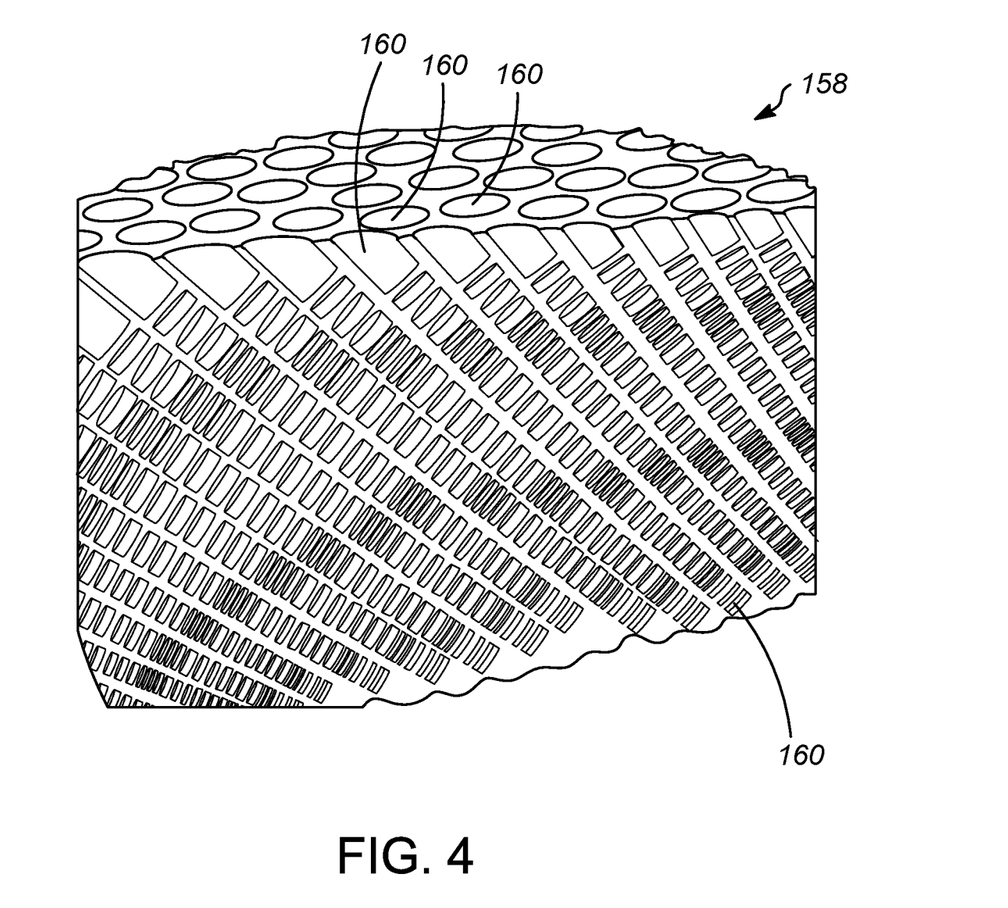
FIG. 4 shows a side cutaway view of an ionic liquid distribution member used in one or more embodiments of the present invention; and, FIG. 5 shows a top and side perspective of another ionic liquid distribution member used in one or more embodiments of the present invention.
Figure 5:
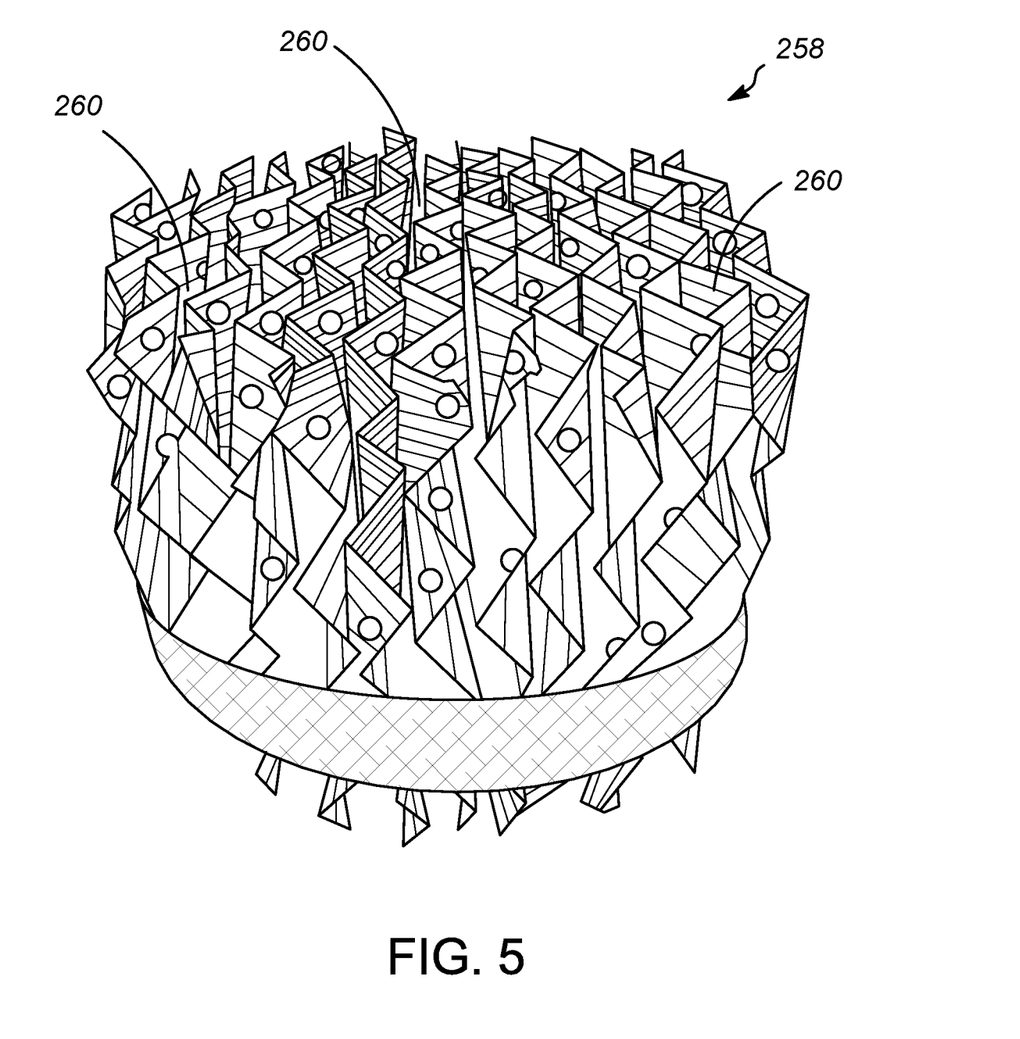

With reference to both FIGS. 4 and 5, the ionic liquid distribution member(s) 54 may comprise structured packing 158, 258. As is known, the structured packing 158, 258 utilizes strips of ribbons, sheets or other structures or designs to provide tortious passageways 160, 260 through the structured packing 158, 258. The tortious passageways 160, 260 of the structured packing 158, 258 facilitates contact between an up-flowing fluid and a down-flowing fluid. Accordingly, as discussed below, ionic liquid may be distributed on a top of the structured packing 158, 258 with a distribution member or manifold (not shown) to ensure even distribution of the ionic liquid. As the ionic liquid flows downward in the tortious passageways 160, 260, it will contact with the hydrocarbons flowing upward tortious passageways 160, 260. Entrained ionic liquid droplets in the hydrocarbons may be removed when contacted with the downward flowing ionic liquid. It should be appreciated that the depicted structured packing 158, 258 in FIGS. 4 and 5 are merely exemplary and that other designs may be used.

Returning to FIG. 1, in order to provide the ionic liquid distribution member 54 with ionic liquid to remove the entailed droplets, a line 66 is provided which may inject ionic liquid into the separation vessel 26 via an inlet 68 for ionic liquid. A pump 70 may be used to pass the ionic liquid to the reaction zone 12, for example as the stream of ionic liquid 20 and may also be used to pass the ionic liquid in the line 66 back into the separation vessel 26 via the inlet 68 for ionic liquid.

Preferably, the inlet 68 of the separation vessel 26 for the ionic liquid is disposed above the ionic liquid distribution member 54, or if there are a plurality of ionic liquid distribution members 54, above the uppermost ionic liquid distribution member 54 of the separation vessel 26. Since the ionic liquid is heavier than the hydrocarbon, the ionic liquid that is passed back into the separation vessel 26 through the inlet 68 for ionic liquid will flow downward. The ionic liquid may then contact the up-flowing hydrocarbons, for example, by forming the layer 56 of ionic liquid on the ionic liquid distribution member 54 through which the up-flowing fluid passes or by traveling through the tortious paths and contacting the up-flowing fluid in a counter-current manner. Other configurations and designs may be utilizes to increase the contact between ionic liquid that is passed back into the separation vessel 26 through the inlet 68 for ionic liquid and the hydrocarbons rising in the separation vessel 26 in order to remove entrained droplets of ionic liquid.

By utilizing the ionic liquid to collect the entrained droplets, less chance of fouling compared to the use of coalescing media or the like. Again, the lower fouling should provide a separation vessel that requires less maintenance. Additionally, the use of the ionic liquid distribution members provides a simpler construction and may utilize existing trays or structured packing designs. The use of these existing designs may allow for less expensive separation vessel including allowing for the retrofitting of existing separation vessels used for different processes. In sum, the invented separation vessels provide advantages by requiring less plot space, utilizing existing designs that may be retrofitted, and provide simpler configurations for recovering entrained ionic liquid.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

SPECIFIC EMBODIMENTS

While the following is described in conjunction with specific embodiments, it will be understood that this description is intended to illustrate and not limit the scope of the preceding description and the appended claims.

A first embodiment of the invention is a separation zone for separating a hydrocarbon phase and an ionic liquid phase, the separation zone comprising a separation vessel having an outlet for an ionic liquid stream, an outlet for a hydrocarbon effluent stream, and, an inlet for an effluent stream; at least one ionic liquid distribution member disposed in the separation vessel between the outlet for the hydrocarbon effluent stream and the inlet for the effluent stream, the at least one ionic liquid distribution member configured to allow up-flowing fluid to pass through the at least one ionic liquid distribution member and contact ionic liquid; and, a line configured to pass ionic liquid to the separation vessel above the at least one ionic liquid distribution member. An embodiment of the invention is one, any or all of prior embodiments in this paragraph up through the first embodiment in this paragraph wherein the separation vessel comprises a vertically orientated separation vessel. An embodiment of the invention is one, any or all of prior embodiments in this paragraph up through the first embodiment in this paragraph further comprising a pump configured to pass the ionic liquid stream from the separation zone to a reaction zone. An embodiment of the invention is one, any or all of prior embodiments in this paragraph up through the first embodiment in this paragraph wherein the pump is also configured to pass ionic liquid to the separation vessel. An embodiment of the invention is one, any or all of prior embodiments in this paragraph up through the first embodiment in this paragraph further comprising a flow directing baffle disposed inside of the separation vessel and configured to change a direction of flow of fluid within the separation vessel. An embodiment of the invention is one, any or all of prior embodiments in this paragraph up through the first embodiment in this paragraph wherein the flow directing baffle is disposed proximate the inlet for the effluent stream. An embodiment of the invention is one, any or all of prior embodiments in this paragraph up through the first embodiment in this paragraph wherein the separation vessel comprises an upper portion with a first diameter and a lower portion with a second diameter being smaller than the first diameter. An embodiment of the invention is one, any or all of prior embodiments in this paragraph up through the first embodiment in this paragraph further comprising a plurality of ionic liquid distribution members disposed in the separation vessel between the outlet for the hydrocarbon effluent stream and the inlet for the effluent stream. An embodiment of the invention is one, any or all of prior embodiments in this paragraph up through the first embodiment in this paragraph wherein the ionic liquid distribution members each comprise a tray, each tray comprising a plurality of passageways for the up-flowing fluid and a downcomer, and wherein the downcomers of adjacent trays are staggered in relation to each other. An embodiment of the invention is one, any or all of prior embodiments in this paragraph up through the first embodiment in this paragraph wherein an uppermost tray is configured to receive ionic liquid via the line configured to pass ionic liquid to the separation vessel.

A second embodiment of the invention is a separation zone for separating a hydrocarbon phase and an ionic liquid phase, the separation zone comprising a vertically orientated separation vessel having an outlet for an ionic liquid stream, an outlet for a hydrocarbon effluent stream, and, an inlet for an effluent stream; a plurality of ionic liquid distribution members disposed in the separation vessel between the outlet for a hydrocarbon effluent stream and the inlet for the effluent stream, each ionic liquid distribution member configured to allow up-flowing fluid to pass through the at least one ionic liquid distribution member and contact ionic liquid; a pump configured to pass the ionic liquid stream from the separation zone to a reaction zone; and, a line configured to pass ionic liquid from the pump back to the vertically orientated separation vessel. An embodiment of the invention is one, any or all of prior embodiments in this paragraph up through the second embodiment in this paragraph wherein the ionic liquid from the line is passed into the vertically orientated separation vessel at a position above an uppermost ionic liquid distribution member and below the outlet for the hydrocarbon effluent stream. An embodiment of the invention is one, any or all of prior embodiments in this paragraph up through the second embodiment in this paragraph wherein each ionic liquid distribution member further comprises a downcomer. An embodiment of the invention is one, any or all of prior embodiments in this paragraph up through the second embodiment in this paragraph wherein the separation vessel comprises an upper portion with a first diameter and a lower portion with a second diameter being smaller than the first diameter. An embodiment of the invention is one, any or all of prior embodiments in this paragraph up through the second embodiment in this paragraph further comprising a flow directing baffle configured to change a direction of flow of fluid within the separation vessel. An embodiment of the invention is one, any or all of prior embodiments in this paragraph up through the second embodiment in this paragraph wherein the separation vessel further comprises a conical portion disposed between the upper portion and the lower portion, and wherein the baffle is disposed in the conical portion.

A third embodiment of the invention is a process for separating an effluent including ionic liquid catalyst, the process comprising passing a reactor effluent stream from a reaction zone to a vertical separation vessel, wherein the separation vessel comprises an upper portion with a first diameter and a lower portion with a second diameter being smaller than the first diameter and a conical portion disposed between the upper portion and the lower portion; separating the reactor effluent stream into an ionic liquid phase and a hydrocarbon phase; passing a first portion of the ionic liquid phase to the reaction zone; and, removing ionic liquid droplets entrained in the hydrocarbon phase in the vertical separation vessel by contacting the hydrocarbon phase with ionic liquid disposed within the upper portion of the vertical separation vessel. An embodiment of the invention is one, any or all of prior embodiments in this paragraph up through the third embodiment in this paragraph wherein a layer of ionic liquid is disposed on an ionic liquid distribution member within the upper portion of the vertical separation vessel. An embodiment of the invention is one, any or all of prior embodiments in this paragraph up through the third embodiment in this paragraph wherein the vertical separation vessel comprises a plurality of ionic liquid distribution members. An embodiment of the invention is one, any or all of prior embodiments in this paragraph up through the third embodiment in this paragraph further comprising passing a second portion of the ionic liquid phase from the lower portion of the vertical separation vessel to the upper portion of the vertical separation vessel.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. A separation zone for separating a hydrocarbon phase and an ionic liquid phase, the separation zone comprising:
    a separation vessel having an outlet for an ionic liquid stream, an outlet for a hydrocarbon effluent stream, and, an inlet for an effluent stream comprising two liquid phases, wherein the separation vessel comprises an upper portion with a first diameter and a lower portion with a second diameter being smaller than the first diameter;
    at least one ionic liquid distribution member disposed in the separation vessel between the outlet for the hydrocarbon effluent stream and the inlet for the effluent stream, the at least one ionic liquid distribution member configured to allow up-flowing fluid to pass through the at least one ionic liquid distribution member and contact ionic liquid; and,
    a line configured to pass ionic liquid to the separation vessel above the at least one ionic liquid distribution member.

2. The separation zone of claim 1 wherein the separation vessel comprises a vertically orientated separation vessel.

3. The separation zone of claim 1 further comprising a pump configured to pass the ionic liquid stream from the separation zone to a reaction zone.

4. The separation zone of claim 3 wherein the pump is also configured to pass ionic liquid to the separation vessel.

5. The separation zone of claim 1 further comprising a flow directing baffle disposed inside of the separation vessel and configured to change a direction of flow of fluid within the separation vessel.

6. The separation zone of claim 5 wherein the flow directing baffle is disposed proximate the inlet for the effluent stream.

7. The separation zone of claim 1 further comprising a flow directing baffle configured to change a direction of flow of fluid from the inlet from a horizontal direction to a downward direction within the separation vessel.

8. The separation zone of claim 1 further comprising a plurality of ionic liquid distribution members disposed in the separation vessel between the outlet for the hydrocarbon effluent stream and the inlet for the effluent stream.

9. The separation zone of claim 8 wherein the ionic liquid distribution members each comprise a tray, each tray comprising a plurality of passageways for the up-flowing fluid and a downcomer, and wherein downcomers of adjacent trays are staggered in relation to each other.

10. The separation zone of claim 9 wherein an uppermost tray is configured to receive ionic liquid via the line configured to pass ionic liquid to the separation vessel.

11. A separation zone for separating a hydrocarbon phase and an ionic liquid phase, the separation zone comprising:
    a vertically orientated separation vessel having an outlet for an ionic liquid stream, an outlet for a hydrocarbon effluent stream, and, an inlet for an effluent stream, wherein the vertically orientated separation vessel comprises an upper portion with a first diameter and a lower portion with a second diameter being smaller than the first diameter;
    a flow directing baffle configured to change a direction of flow of fluid injected via the inlet from a horizontal direction to a downward direction;
    a plurality of ionic liquid distribution members disposed in the separation vessel between the outlet for a hydrocarbon effluent stream and the inlet for the effluent stream, each ionic liquid distribution member configured to allow up-flowing fluid to pass through the liquid distribution member and contact ionic liquid;
    a pump configured to pass the ionic liquid stream from the separation zone to a reaction zone; and,
    a line configured to pass ionic liquid from the pump back to the vertically orientated separation vessel.

12. The separation zone of claim 11 wherein the ionic liquid from the line is passed into the vertically orientated separation vessel at a position above an uppermost ionic liquid distribution member and below the outlet for the hydrocarbon effluent stream.

13. The separation zone of claim 12 wherein each ionic liquid distribution member further comprises a downcomer.

14. The separation zone of claim 11 wherein the separation vessel further comprises a conical portion disposed between the upper portion and the lower portion, and wherein the flow directing baffle is disposed in the conical portion.

15. A process for separating an effluent including ionic liquid catalyst, the process comprising:
    passing a reactor effluent stream from a reaction zone to a vertical separation vessel, wherein the separation vessel comprises an upper portion with a first diameter and
a lower portion with a second diameter being smaller than the first diameter and a conical portion disposed between the upper portion and the lower portion;
separating the reactor effluent stream into an ionic liquid phase and a hydrocarbon phase; passing a first portion of the ionic liquid phase to the reaction zone; and,
removing ionic liquid droplets entrained in the hydrocarbon phase in the vertical separation vessel by contacting the hydrocarbon phase with ionic liquid disposed within the upper portion of the vertical separation vessel.

16. The process of claim 15 wherein a layer of ionic liquid is disposed on an ionic liquid distribution member within the upper portion of the vertical separation vessel.

17. The process of claim 15 wherein the vertical separation vessel comprises a plurality of ionic liquid distribution members.

18. The process of claim 16 further comprising passing a second portion of the ionic liquid phase from the lower portion of the vertical separation vessel to the upper portion of the vertical separation vessel.

* * * * *